(12) United States Patent
Belmont

(10) Patent No.: US 8,178,692 B2
(45) Date of Patent: May 15, 2012

(54) METHODS FOR PRODUCTION OF 1,2,4-TRIAZOL-3-ONE

(75) Inventor: Stephen E. Belmont, Baton Rouge, LA (US)

(73) Assignee: Albemarle Corporation, Baton Rouge, LA (US)

( * ) Notice: Subject to any disclaimer, the term of this patent is extended or adjusted under 35 U.S.C. 154(b) by 119 days.

(21) Appl. No.: 12/674,210

(22) PCT Filed: Sep. 18, 2008

(86) PCT No.: PCT/US2008/076827
§ 371 (c)(1),
(2), (4) Date: Feb. 19, 2010

(87) PCT Pub. No.: WO2009/039257
PCT Pub. Date: Mar. 26, 2009

(65) Prior Publication Data
US 2011/0263867 A1    Oct. 27, 2011

(51) Int. Cl.
*C07D 249/08* (2006.01)
*C07D 401/06* (2006.01)
(52) U.S. Cl. .................................................. 548/262.2
(58) Field of Classification Search ................ 548/262.2, 548/263.2
See application file for complete search history.

(56) References Cited

U.S. PATENT DOCUMENTS

| 4,733,610 A | 3/1988 | Lee et al. |
| 4,927,940 A | 5/1990 | Boudakian et al. |
| 5,112,983 A * | 5/1992 | Boudakian et al. ........ 548/263.2 |
| 2011/0201822 A1* | 8/2011 | Belmont et al. ........... 548/263.2 |

FOREIGN PATENT DOCUMENTS

EP    0 210 881    2/1987

OTHER PUBLICATIONS

Kroeger et al., Chemische Berichte, vol. 98, Issue 9, pp. 3034-3039, 1965.*
Zhang, Jianguo, et al; "The Crystal and Computed Structure of 1,2,4-Triazol-5-One"; Journal of Heterocyclic Chemistry, vol. 43, pp. 503-508; 2006.
Chipen, G. I., et al; "1,2,4-Triazol-3-One and Its Nitro and Amino Derivatives"; Chemistry of Heterocyclic Compounds, vol. 2, No. 1, pp. 79-83; 1966.

* cited by examiner

*Primary Examiner* — Susannah Chung
(74) *Attorney, Agent, or Firm* — Marcy M. Hoefling; Jeremy J. Kliebert; James A. Jubinsky

(57) ABSTRACT

Novel methods for producing 1,2,4-triazol-3-one from semicarbazide hydrochloride and formic acid are provided. In methods of this invention, ethanol is used in removal of unreacted formic acid to increase yield and purity of produced 1,2,4-triazol-3-one.

5 Claims, 1 Drawing Sheet

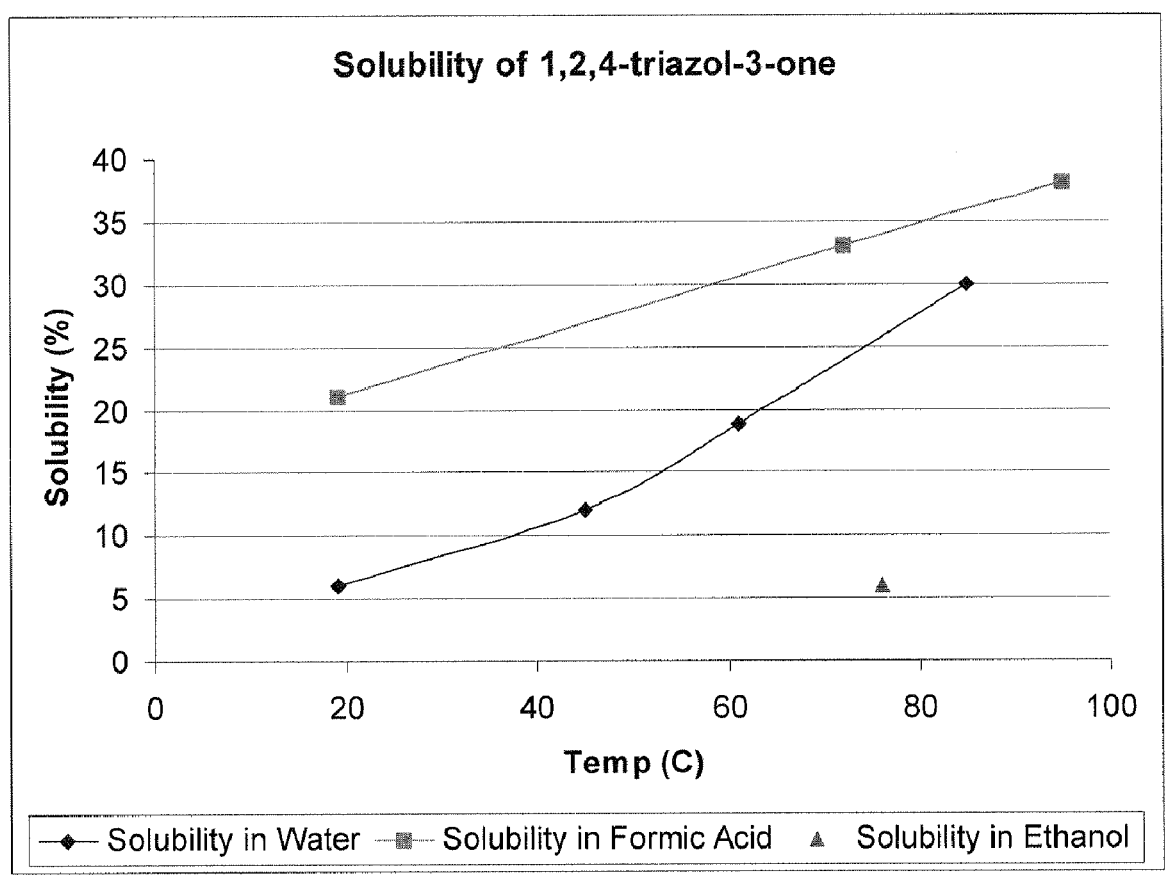

METHODS FOR PRODUCTION OF 1,2,4-TRIAZOL-3-ONE

BACKGROUND 1,2,4-triazol-3-one is useful as a raw material for production of nitro-1,2,4-triazol-3-one [(NTO) ($C_2H_2N_4O_2$)], a known explosive with high energy and low sensitivity. NTO is widely used in explosive formulations and gas generators for automobile inflatable airbag systems.

It would be beneficial to the defense industry and to the automobile airbag industry if there were methods for production of 1,2,4-triazol-3-one that provided commercially acceptable yield and product purity.

THE INVENTION

This invention meets the above-described needs by providing novel methods for production of 1,2,4-triazol-3-one. Methods according to this invention can produce 1,2,4-triazol-3-one having a purity of at least about 98.5% at yields of up to about 76%.

Methods of this invention can comprise (i) combining semicarbazide hydrochloride and formic acid to form an initial composition, optionally in amounts such that the formic acid is combined in up to about 7 equivalents as to the semicarbazide hydrochloride, (ii) heating the initial composition to a temperature of about 70° C. to about 105° C. and maintaining the temperature for at least about 1 hour to form a product composition, (iii) distilling the product composition to remove at least a portion of unreacted formic acid and form a concentrated product composition, optionally recovering at least a portion of the removed unreacted formic acid for use in (i), (iv) combining the concentrated product composition and ethanol and, optionally, heating to at least about 40° C., optionally over a period of at least about 10 minutes, (v) cooling the concentrated product composition to at least about 20° C., (vi) collecting crude 1,2,4-triazol-3-one from the concentrated crude product composition, combining with water, and heating to a crystallization temperature high enough to dissolve crude 1,2,4-triazol-3-one, e.g., at least about 70° C., to form a product solution, (vii) cooling the product solution to lower than about 10° C., optionally over a period of at least about 2.5 hours, and (viii) collecting recrystallized 1,2,4-triazol-3-one from the product solution. The recrystallized 1,2,4-triazol-3-one can be dried, e.g., under vacuum at an appropriate temperature, e.g., 40° C.

FIGURES

The invention will be better understood by reference to the FIGURE (FIG. 1), which illustrates the solubility of 1,2,4-triazol-3-one in water and in formic acid.

DESCRIPTION

Various means for heating, cooling, maintaining temperatures, distilling, recovering distilled unreacted formic acid, and collecting produced product are known to those skilled in the art. This invention is not limited to the means described in the description and example provided herein.

According to methods of this invention, semicarbazide hydrochloride can be reacted with formic acid to produce the 1,2,4-triazol-3-one. The semicarbazide hydrochloride and the formic acid can be combined in amounts such that the amount of formic acid is only up to about 7 molar equivalents as to the semicarbazide hydrochloride. The semicarbazide hydrochloride and formic acid initial composition can be heated to a temperature of at least about 70° C., e.g., about 95° C. to about 105° C., and maintained at the temperature for at least about 1 hour to produce crude 1,2,4-triazol-3-one. While the reaction is typically conducted at atmospheric pressure, greater than atmospheric pressure may be employed if desired. The reaction time can vary up to several hours or more, depending upon the amounts of formic acid and semicarbazide hydrochloride combined.

After the desired reaction time, the product composition that was formed can be cooled to about 50° C. to about 40° C. Cooling can be accomplished by direct cooling or by evaporative cooling, e.g., under vacuum. After the desired reaction time or after cooling, the product composition can be distilled to remove at least a portion of unreacted formic acid; some water can also be removed during the distillation. As desired, at least a portion of the unreacted formic acid can be recovered for use in reacting with semicarbazide hydrochloride. The concentrated product composition can be slurried in ethanol and, if desired, the slurry can be heated to at least about 40° C., over a period of at least about 10 minutes, or for as long as is needed to dissolve any remaining unreacted formic acid in the concentrated product composition. If heated, the slurry can then be cooled to at least about 20° C. Crude 1,2,4-triazol-3-one can be collected from the concentrated product composition.

The crude 1,2,4-triazol-3-one can be recrystallized by adding (combining with) water to form a crude solution and heating the crude solution to at least about 70° C. to about 100° C. to dissolve the solids, followed by cooling. Use of water as the recrystallization solvent assists with removal of chlorides from the distilled product. Produced solid 1,2,4-triazol-3-one can be collected on a filter, washed, e.g., with water, and dried under vacuum at an appropriate temperature, e.g., 40° C., or other appropriate temperature. The ratio of recrystallization solvent, i.e., water, to product mass (isolated dried solid 1,2,4-triazol-3-one) can be as low as 1.75.

Methods of this invention are particularly advantageous in that they allow for removal of unreacted formic acid from the product composition and the concentrated product composition. Refer to the FIGURE (FIG. 1), which illustrates that 1,2,4-triazol-3-one is much more soluble in formic acid than it is in water. Thus removal of unreacted formic acid leads to a higher yield of the desired product, 1,2,4-triazol-3-one, than would otherwise be achieved. The FIGURE also illustrates that the difference in solubility between water and formic acid is greater at lower temperatures. The FIGURE also shows a single data point for solubility of the product in ethanol, i.e., 6% solubility at 76° C., which is much lower than the solubility in either water or formic acid. The purpose of the ethanol slurry is to dissolve away the remaining formic acid and water, while forcing the 1,2,4-triazol-3-one product out of solution by using a solvent (ethanol) in which it has very low solubility. The solubility in water as shown in the FIGURE shows the advantage of recrystallizing in water (with as little formic acid as possible), as described herein.

The following example is illustrative of the principles of this invention. It is understood that this invention is not limited to any one specific embodiment exemplified herein, whether in the example or the remainder of this patent application.

EXAMPLE

Semicarbazide hydrochloride (142 g., 1.27 mol) and 96% formic acid (0.40 kg, 8.7 mol) were added to a 1-L 4-neck RB flask with mechanical stirrer, condenser, thermocouple, and caustic scrubber attached. The reaction was heated to 105° C. for 1 hour. During the heating (starting at about 70° C.) there was considerable HCl gas evolution into the scrubber. After cooling to 45-50° C., the bulk of the formic acid (and water byproduct) was distilled off on a rotovap with a 40° C. bath at 25-35 mm vacuum. The white slurry was taken up in ethanol (50 mL), heated to 40° C. for 10 minutes, and cooled to 20° C. Crude product was collected on a sintered glass funnel and washed with ethanol (30 mL). The crude product and water (150 mL) were heated to 95° C. to dissolve the solids and cooled to 5° C. over 2.5 hours. The recrystallized product was collected in a filter, washed with water (30 mL), and dried at 40° C. under high vacuum, affording 78.9 g (72%) of a white, crystalline solid (quant NMR=98.6%).

It is to be understood that the reactants and components referred to by chemical name or formula anywhere in the specification or claims hereof, whether referred to in the singular or plural, are identified as they exist prior to being combined with or coming into contact with another substance referred to by chemical name or chemical type (e.g., another reactant, a solvent, or etc.). It matters not what chemical changes, transformations and/or reactions, if any, take place in the resulting combination or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a combination to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, combined, blended or mixed with one or more other substances, components and/or ingredients in accordance with the present disclosure. Whatever transformations, if any, which occur in situ as a reaction is conducted is what the claim is intended to cover. Thus the fact that a substance, component or ingredient may have lost its original identity through a chemical reaction or transformation during the course of contacting, combining, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof. As will be familiar to those skilled in the art, the terms "combined", "combining", and the like as used herein mean that the components that are "combined" or that one is "combining" are put into a container with each other. Likewise a "combination" of components means the components having been put together in a container.

While the present invention has been described in terms of one or more preferred embodiments, it is to be understood that other modifications may be made without departing from the scope of the invention, which is set forth in the claims below.

What is claimed is:

1. A method for producing 1,2,4-triazol-3-one comprising (i) combining semicarbazide hydrochloride and formic acid to form an initial composition, (ii) heating the initial composition to a temperature of at least 70° C. and maintaining the temperature for at least 1 hour to form a product composition, (iii) distilling the product composition to remove a portion of unreacted formic acid and form a concentrated product slurry, (iv) slurrying the concentrated product slurry in ethanol to form an ethanol slurry, and heating the ethanol slurry to at least 40° C. over a period of at least 10 minutes, (v) collecting crude 1,2,4-triazol-3-one from the ethanol slurry, (vi) combining the crude 1,2,4-triazol-3-one with water and heating to dissolve crude 1,2,4-triazol-3-one to form a product solution, (vii) cooling the product solution to lower than 10° C., and (viii) collecting recrystallized 1,2,4-triazol-3-one from the product solution.

2. The method of claim 1 wherein the formic acid is combined in up to 7 equivalents as to the semicarbazide hydrochloride.

3. The method of claim 1 wherein the cooling is conducted over a period of at least 2.5 hours.

4. The method of claim 1 further comprising (ix) drying the recrystallized 1,2,4-triazol-3-one under vacuum.

5. A method for producing 1,2,4-triazol-3-one comprising (i) combining semicarbazide hydrochloride and formic acid to form an initial composition in amounts such that the formic acid is combined in up to 7 equivalents as to the semicarbazide hydrochloride, (ii) heating the initial composition to a temperature of at least 70° C. and maintaining the temperature for at least 1 hour to form a product composition, (iii) distilling the product composition to remove at least a portion of unreacted formic acid and form a concentrated product slurry, (iv) slurrying the concentrated product slurry in ethanol to form an ethanol slurry, and heating the ethanol slurry to at least 40° C. over a period of at least 10 minutes, (v) collecting crude 1,2,4-triazol-3-one from the ethanol slurry, (vi) combining the crude 1,2,4-triazol-3-one with water, and heating to at least 70° C. to form a product solution, (vii) cooling the product solution to lower than 10° C. over a period of at least 2.5 hours, (viii) collecting recrystallized 1,2,4-triazol-3-one from the product solution, and (ix) drying the recrystallized 1,2,4-triazol-3-one.

* * * * *